Figure 1:
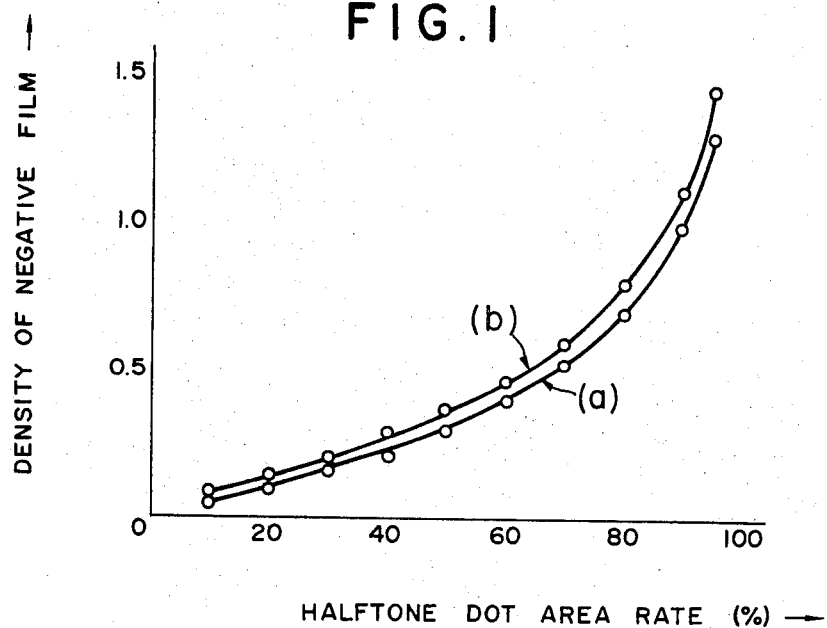

United States Patent [19]

Yonekura

[11] 4,400,617
[45] Aug. 23, 1983

[54] CORRECTION CIRCUIT OF A HALFTONE DOT AREA RATE DETECTOR

[75] Inventor: Yasuhiro Yonekura, Hikone, Japan

[73] Assignee: Dainippon Screen Seizo Kabushiki Kaisha, Kyoto, Japan

[21] Appl. No.: 320,096

[22] Filed: Nov. 10, 1981

[30] Foreign Application Priority Data

Dec. 1, 1980 [JP] Japan .............................. 55-168096

[51] Int. Cl.³ .......................................... H01J 40/14
[52] U.S. Cl. ........................... 250/214 A; 250/559
[58] Field of Search ................... 250/214 A, 206, 559; 356/444

[56] References Cited

U.S. PATENT DOCUMENTS 4,259,570  3/1981  Leonard ......................... 250/214 A Primary Examiner—David C. Nelms
Assistant Examiner—Darwin R. Hostetter
Attorney, Agent, or Firm—Poms, Smith, Lande & Rose

[57] ABSTRACT

A correction circuit of a halftone dot area rate detector wherein a relation between a detected halftone dot area rate and a light transmittance or reflectance of an object obtained by a halftone photography is approximately expressed by a turning curve having at least one turning point, which comprises line segments, by using a turning point correction circuit comprising an inverting amplifying circuit, wherein another inverting amplifying circuit is coupled in parallel with the turning point correction circuit, and wherein a potensiometer couples the outputs of the two circuits and outputs a signal corresponding to a correction amount.

2 Claims, 9 Drawing Figures

United States Patent [19]

Yonekura

[11] 4,400,617
[45] Aug. 23, 1983

[54] CORRECTION CIRCUIT OF A HALFTONE DOT AREA RATE DETECTOR

[75] Inventor: Yasuhiro Yonekura, Hikone, Japan

[73] Assignee: Dainippon Screen Seizo Kabushiki Kaisha, Kyoto, Japan

[21] Appl. No.: 320,096

[22] Filed: Nov. 10, 1981

[30] Foreign Application Priority Data

Dec. 1, 1980 [JP] Japan ................................ 55-168096

[51] Int. Cl.³ ............................................. H01J 40/14
[52] U.S. Cl. .................................. 250/214 A; 250/559
[58] Field of Search ................... 250/214 A, 206, 559; 356/444

[56] References Cited

U.S. PATENT DOCUMENTS 4,259,570 3/1981 Leonard .......................... 250/214 A Primary Examiner—David C. Nelms
Assistant Examiner—Darwin R. Hostetter
Attorney, Agent, or Firm—Poms, Smith, Lande & Rose

[57] ABSTRACT

A correction circuit of a halftone dot area rate detector wherein a relation between a detected halftone dot area rate and a light transmittance or reflectance of an object obtained by a halftone photography is approximately expressed by a turning curve having at least one turning point, which comprises line segments, by using a turning point correction circuit comprising an inverting amplifying circuit, wherein another inverting amplifying circuit is coupled in parallel with the turning point correction circuit, and wherein a potensiometer couples the outputs of the two circuits and outputs a signal corresponding to a correction amount.

2 Claims, 9 Drawing Figures

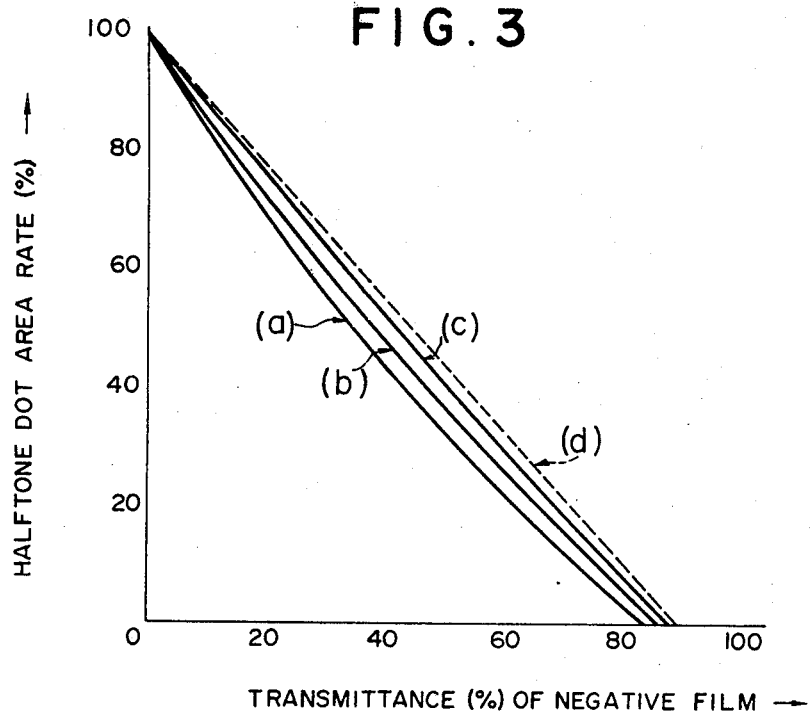
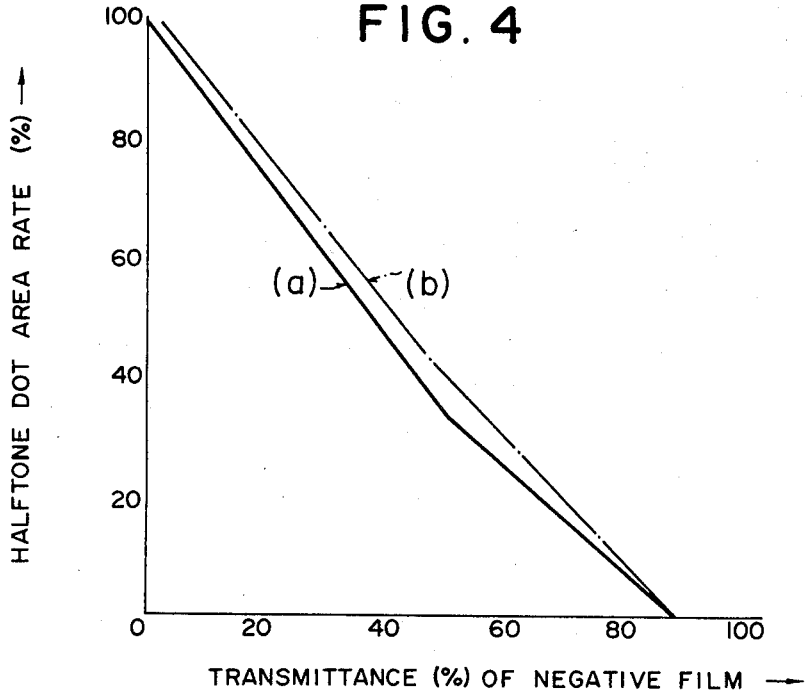

CORRECTION CIRCUIT OF A HALFTONE DOT AREA RATE DETECTOR

BACKGROUND OF THE INVENTION

The present invention relates to a correction circuit of a halftone dot area rate detector which detects a light transmittance or reflectance of a halftone negative or positive film, printed matter, or the like.

Generally, the finish color and tone of a printed matter depend on halftone dot area rates of halftone negative or positive films, hereinafter referred to as a halftone film in short, used in a photographic plate making process prior to a printing process. Therefore, the control of the halftone dot area rate of the halftone film is very important. In the prior art, this control is carried out by using a densitometer.

Now, assuming that the halftone dot area rate and the light transmittance of the halftone film are A and T, the following equation is obtained.

$$A = 1 - T \quad (1)$$

Then, if the density of the halftone film at a point wherein the light transmittance is detected, is defined to D, the following equation is obtained.

$$D = -\log T \text{ or } T = 10^{-D} \quad (2)$$

From these equations (1) and (2), the following equation is obtained.

$$D = \log \frac{1}{1 - A} \quad (3)$$

Hence, when the density value D of the halftone film, which is obtained by subtracting a basic density from its detected density, is 0.6, the light transmittance T is calculated according to the equation (2) to obtain $10^{-0.6} = 0.25$, and the halftone dot area rate A is calculated according to the equation (1) to obtain $1 - 0.25 = 0.75$. This value is considered to be 75% of the halftone dot area rate at the detecting point of the halftone film.

However, usually, the actual halftone dot somewhat includes a fringe around the periphery. Particularly, in the first halftone film obtained by the halftone photography, the halftone dots include the fringes to the considerable extent, which is designated as "soft dot", and therefore in this case the formula (1) is not applicable.

Further, the fringes of the halftone dots vary depending on a reproducible density range of a contact screen used for the halftone photography, screen ruling, gamma characteristics of a lithographic film under the developing conditions, and the like.

To the contrary, when such conditions are not changed, the influences by the fringes are stable. Hence, in a conventional method, the density value detected by the densitometer is corrected by subtracting a fixed number therefrom, and then the halftone dot area rate is determined according to the fact that the corrected density value may satisfy the above equations (1)-(3).

However, in fact, as clearly shown by two curves (a) and (b) which are obtained by a calculation according to the equation (3) and an experience, and which express a relation between a halftone dot area rate and a density of a halftone negative film, obtained by subtracting a basic density from its detected density, in FIG. 1, the correction values or the differences between the two curves (a) and (b) at the halftone dot area rates of around 5%, 50% and 95% exist. Therefore, such a conventional correction method can not effect a correct halftone dot area rate.

In this method, in order to improve the detecting accuracy, a very complicated conversion operation between the detected density of the halftone negative film and the halftone dot area rate is required, which is in practice very inconvenience.

A so-called halftone dot area rate detector has been proposed. It calculates the halftone dot area rate basically according to the above equation (1) and displays it. That is, it detects the light transmittance of the halftone film and then detects the halftone dot area rate therefrom. In this case, the influence of the fringe is considered in the followings.

That is, in a halftone dot (dead point) having a halftone dot area rate less than the minimum representing halftone dot area rate, wherein the representing halftone dot area rate of 100% is obtained in the halftone photography, the light is absorbed by an original picture to a certain extent more than that corresponding to the basic density, i.e. the light transmittance is somewhat smaller than that corresponding to the basic density.

However, in such a halftone dot area rate detector, the halftone dot area rate of such a halftone dot (dead point) having a halftone dot area rate less than the minimum representing halftone dot area rate is expressed to 0% or not more than 0%, as suggested above, and only the halftone dot area rates of the halftone dots having at least the minimum representing halftone dot area rate which is obtained in the halftone photography, are indicated.

Figure 2:
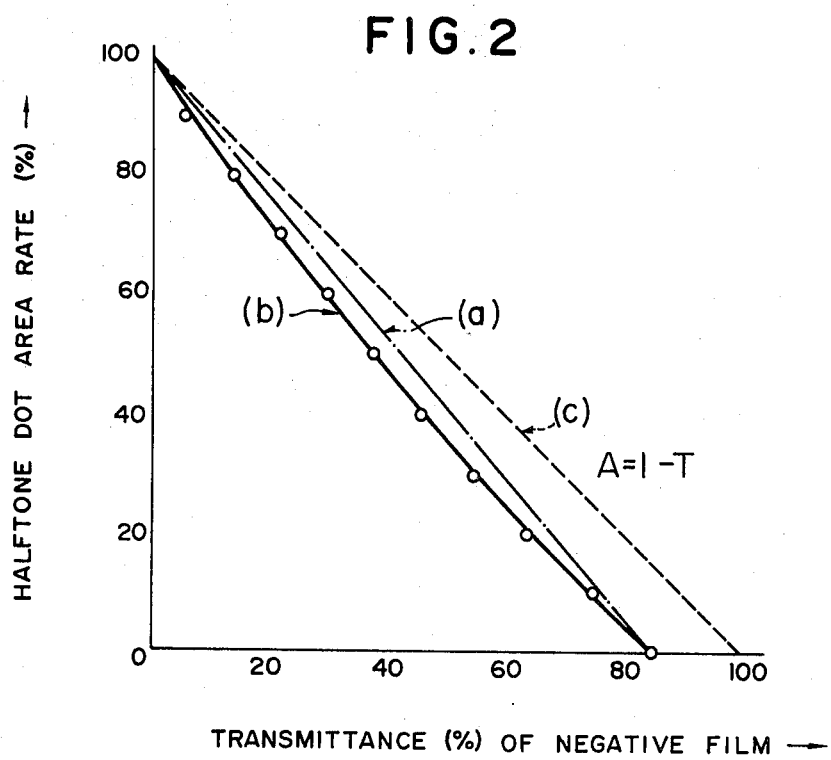
Figure 5:
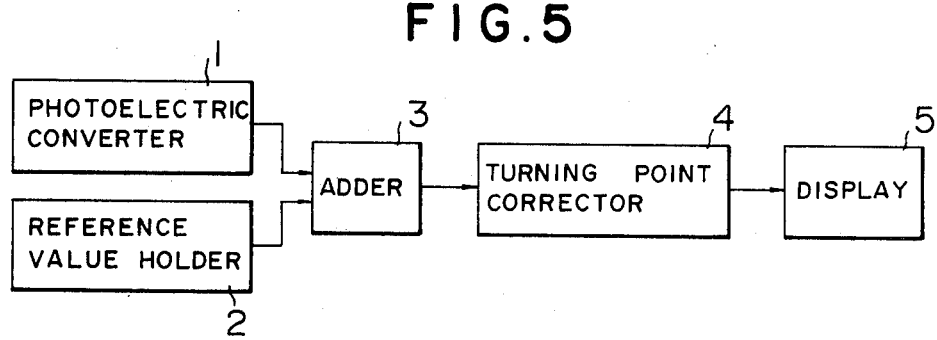
Figure 6:
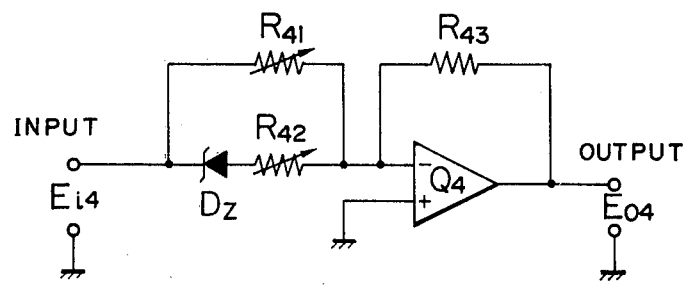
Figure 7:
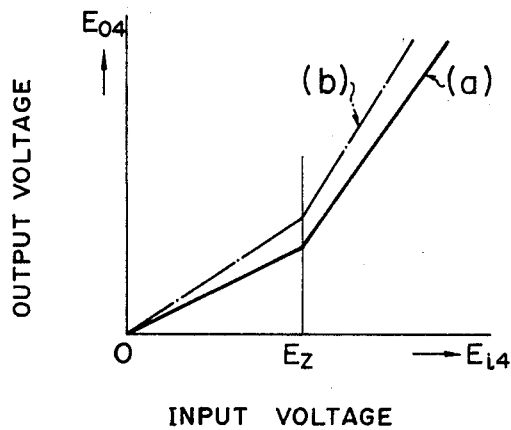
Figure 8:
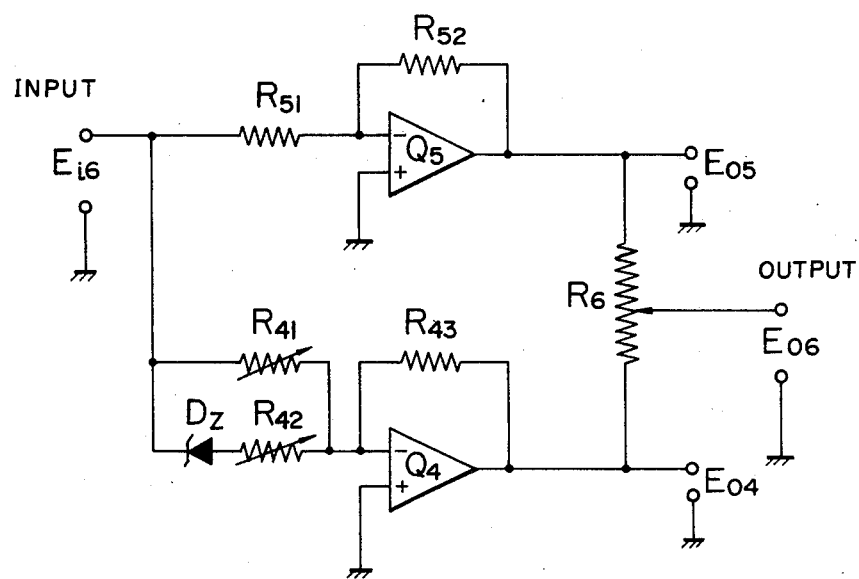
Figure 9:
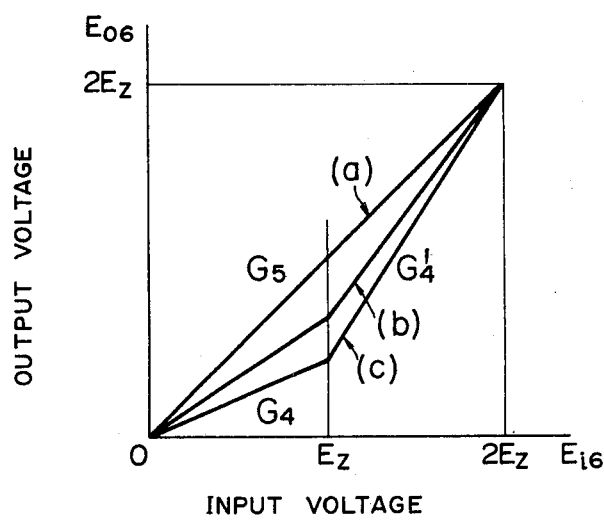

For example, in the halftone negative film having a basic density of 0.05 (a light transmittance of 89%), when the light transmittance at the minimum representing halftone dot area rate is 85% under the influence of the fringe, the halftone dot area rates of the halftone dots having a light transmittance of more than 85% are indicated to 0%, and the halftone dot area rates of the other halftone dots having a light transmittance of at most 85% is obtained from an approximation line which is obtained by connecting the two points by a line, wherein the halftone dot area rates are 100% and 0% when the light transmittances are 0% and 85%, as shown by a line (a) in FIG. 2 which shows curves which exhibit the relations between the light transmittance of the halftone negative film and the halftone dot area rate.

Therefore, in this conventional halftone dot area rate detector, the influence of the fringe is not taken into consideration in the intermediate halftone dot area rates, and thus the actual values detected, which are represented by a curve (b) of FIG. 2, are not coincident with those expressed by the line (a) of FIG. 2, for example, a difference of several percent occurs around the light transmittance of 50%.

In particular, when the halftone dot area rate is corrected by a dot etching or dot reduction, since it is often evaluated by the naked eye, around the light transmittance of 50% where it is easily observed by the naked eye, it is not desirable that the difference between the actual value and the value appeared on the scale of the halftone dot area rate detector occurs. A broken line (c) of FIG. 2 represents the equation (1) (A = 1 − T).